United States Patent
Roundhill et al.

(10) Patent No.: US 6,283,919 B1
(45) Date of Patent: Sep. 4, 2001

(54) ULTRASONIC DIAGNOSTIC IMAGING WITH BLENDED TISSUE HARMONIC SIGNALS

(75) Inventors: David N. Roundhill, Bothell; Michalakis Averkiou, Kirkland; Jeffry E. Powers, Bainbridge Is., all of WA (US)

(73) Assignee: ATL Ultrasound, Bothell, WA (US)

( * ) Notice: Subject to any disclaimer, the term of this patent is extended or adjusted under 35 U.S.C. 154(b) by 0 days.

(21) Appl. No.: 09/247,343

(22) Filed: Feb. 8, 1999

Related U.S. Application Data

(62) Division of application No. 08/943,546, filed on Oct. 3, 1997, now Pat. No. 5,879,303
(60) Provisional application No. 60/032,771, filed on Nov. 26, 1996.

(51) Int. Cl.[7] ........................................ A61B 8/00
(52) U.S. Cl. ................................ 600/447; 600/458
(58) Field of Search .................... 600/440–441, 600/443, 447, 458

(56) References Cited

U.S. PATENT DOCUMENTS

| | | |
|---|---|---|
| 4,702,258 | 10/1987 | Nicolas . |
| 4,714,846 | 12/1987 | Pesque . |
| 5,158,071 | 10/1992 | Umemura . |
| 5,255,683 | 10/1993 | Monaghan . |
| 5,410,516 | 4/1995 | Uhlendorf et al. . |
| 5,415,171 | 5/1995 | Goh . |
| 5,419,328 | 5/1995 | Goh . |
| 5,435,311 | 7/1995 | Umemura . |
| 5,526,816 * | 6/1996 | Arditi .................. 600/458 |
| 5,608,690 | 3/1997 | Hossack et al. . |
| 5,740,128 | 4/1998 | Hossack et al. . |
| 5,897,500 * | 4/1999 | Zhao .................. 600/443 |
| 6,048,316 * | 4/2000 | Zhao et al. ............ 600/447 |

FOREIGN PATENT DOCUMENTS

| | | |
|---|---|---|
| WO98/20361A1 | 5/1998 | (WO) . |
| WO98/46169 | 10/1998 | (WO) . |
| WO98/57483 | 12/1998 | (WO) . |

OTHER PUBLICATIONS

Starritt, Evidence for ultrasonic finite amplitude distortion in muscle using medical equipment, JASA 77(1), Jan. 1985 at 302–06.

Muir, Prediction of nonlinear acoustic effects at biomedical frequencies and intensities, Ult. in Med. & Biol., Bol. 6 at 345–57 (1980).

Carstensen, Demonstration of nonlinear acoustical effects at biomedical frequencies and intensities, Ult. in Med. & Biol. vol. 6 at 359–68 (1980).

Starritt, The development of harmonic distrotion in pulsed finite–amplitude ultrasound passing through passing through liver, Phys. Med. Biol., vol. 31, No. 12, 1401–09 (1986).

Ward, Non–linear propagation applied to the improvement of lateral resolution in medical ultasound scanners, 1995 World Cong. on Ult. at 965–68.

Law, Ultrasonic determination of thre nonlinearity parameter B/A for biological media, JASA 69(4), Aprli 1981 at 1210–12.

(List continued on next page.)

Primary Examiner—Francis J. Jaworski
(74) Attorney, Agent, or Firm—W. Brinton Yorks, Jr.

(57) ABSTRACT

An ultrasonic diagnostic imaging system and method are described which produce tissue harmonic images containing both fundamental and harmonic frequency components. Such a blended image takes advantage of the performance possible with the two types of ultrasonic echo information and can advantageously reduce near field clutter while improving signal to noise performance in the far field of the image.

41 Claims, 10 Drawing Sheets

OTHER PUBLICATIONS

Dunn, et al., Nonlinear Ultrasonic Wave Propagation in Biological Materials, 1981 Ultrasonics Symposium at 527–32 (IEEE).

Muir, Nonlinear Effects In Acoustic Imaging, Acoustical Imaging, vol. 9 at 93–109 (Plenum Press, NYC, 1980).

Ichida et al., Imaging the Nonlinear Parameter of a Medium, Ultrasonic Imaging, vol. 5 at 295–99 (Academic Press, 1983).

Christopher, Finite Amplitude Distortion–Based Inhomogeneous Pulse Echo Ultrasonic Imaging, IEEE Tras. Ult., Ferro. & Freq. Contr., vol. 44, Jan. 1997 at 123 and particularly p. 138.

Burns et al., Harmonic Power Mode Doppler Using Microbubble Contrast Agents, J.E.M.U., vol. 16, No. 4 at 132–42 (Masson, Paris, 1995).

Burns, et al., Harmonic Imaging Principles and Preliminary Results, Angiology vol. 47, No.7. Part 2 at 563–574 (Jul. 1996 New York).

Burns, Presentation of Papers Nos. 241, 243, 1046, 1438, 1682, 166, 169 Supplements to Radiology (Nov. 1992, vol. 185, Nov. 1993, vol. 193, Nov. 1995, vol. 197, Nov. 1996, vol. 201).

Averkiou, et al., Measurements of Harmonic Generation in a Focused Finite–Amplitude Sound Beam, J. Acoust. Soc. Am. 98(6) at 3439–42 (Dec. 1995).

Ward, et al., Nonlinear Propagation Applied to the improvement of Resolution in Diagnostic Medical Ultrasound, J. Acoust. Soc. Am. 101(1) at 143–54 (Jan. 1997), particularly p. 143.

Schrope, et al., Simulated Capillary Blood Flow Measurement Using a Nonlinear Ultrasonic Contrast Agent, Ultasonic Imaging 13 at 134–58 (Acu. Press 1992).

Schrope, et al., Second Harmonic Ultrasonic Blood Perfusion Measurement, Ult. in Med. & Biol. 19(7) at 567–79 (Pergamon Press 1993).

* cited by examiner

ULTRASONIC DIAGNOSTIC IMAGING WITH BLENDED TISSUE HARMONIC SIGNALS

This is a divisional application of U.S. patent application Ser. No. 08/943,546, filed Oct. 3, 1997 and entitled "ULTRASONIC DIAGNOSTIC IMAGING OF RESPONSE FREQUENCY DIFFERING FROM TRANSMIT FREQUENCY" now U.S. Pat. No. 5,879,303, which claims the benefit of U.S. Provisional Application No. 60/032,771 filed Nov. 26, 1996.

This invention relates to ultrasonic diagnosis and imaging of the body and, in particular, to new methods and apparatus for ultrasonically imaging with a response frequency which differs from the transmitted frequency.

Ultrasonic diagnostic imaging systems have been used to image the body with the enhancement of ultrasonic contrast agents. Contrast agents are substances which are biocompatible and exhibit uniquely chosen acoustic properties which return readily identifiable echo signals in response to insonification. Contrast agents can have several properties which enables them to enhance an ultrasonic image. One is the nonlinear characteristics of many contrast agents. Agents have been produced which, when insonified by an ultrasonic wave at one frequency, will exhibit resonance modes which return energy at other frequencies, in particular, harmonic frequencies. A harmonic contrast agent, when insonified at a fundamental frequency, will return echoes at the second, third, fourth, and higher harmonics of that frequency.

It has been known for some time that tissue and fluids also have inherent nonlinear properties. Tissue and fluids will, even in the absence of a contrast agent, develop and return their own non-fundamental frequency echo response signals, including signals at harmonics of the fundamental. Muir and Carstensen explored these properties of water beginning in 1980, and Starritt et al. looked at these properties in human calf muscle and excised bovine liver.

While these non-fundamental frequency echo components of tissue and fluids are generally not as great in amplitude as the harmonic components returned by harmonic contrast agents, they do exhibit a number of characteristics which may be advantageously used in ultrasonic imaging. One of us (M. Averkiou) has done extensive research into these properties in work described in his doctoral dissertation. In this exposition and other research, the present inventors have seen that the main lobe of a harmonic beam is narrower than that of its fundamental, which they have found has implications for clutter reduction when imaging through narrow orifices such as the ribs. They have seen that the sidelobe levels of a harmonic beam are lower than the corresponding sidelobe levels of the fundamental beam, which they have found has implications for off-axis clutter reduction. They have also seen that harmonic returns from the near field are also relatively less than returning energy at the fundamental frequency, which they have found has implications for near field clutter rejection. As will be seen, these properties may be exploited in the methods and constructed embodiments of the present invention.

In accordance with the principles of the present invention, an ultrasonic imaging system and method are provided for imaging tissue and fluids from response frequencies which differ from the transmitted frequency, in particular echoes returned from the tissue or fluids at a harmonic of a transmitted fundamental frequency. The imaging system comprises a means for transmitting an ultrasonic wave at a fundamental frequency, means for receiving echoes at a harmonic frequency, and an image processor for producing an ultrasonic image from the harmonic frequency echoes.

In a preferred embodiment of the present invention the transmitting and receiving means comprise a single ultrasonic probe. In accordance with a further aspect of the present invention, the probe utilizes a broadband ultrasonic transducer for both transmission and reception.

In accordance with yet another aspect of the present invention, partially decorrelated components of received harmonic echoes are produced and utilized to remove artifacts from the harmonic image, providing clearly defined images of tissue boundaries such as that of the endocardium. In a preferred embodiment the partially decorrelated components are produced by processing the harmonic echoes through different passbands.

The methods of the present invention include the use of harmonic echoes to reduce near-field or multipath clutter in an ultrasonic image, such as that produced when imaging through a narrow acoustic window such as the ribs. In accordance with yet a further aspect of the present invention, harmonic and fundamental echoes are blended in a common image to reduce clutter, image at appreciable depths, and overcome the effects of depth-dependent attenuation.

In the drawings:

FIG. 1 illustrates in block diagram form an ultrasonic diagnostic imaging system constructed in accordance with the principles of the present invention;

FIGS. 2, 3, 4, and 5 illustrate certain properties of harmonic echoes which may be advantageously applied to ultrasonic imaging applications; and FIGS. 6 and 7 illustrate passband characteristics used to explain the performance of the embodiment of FIG. 1;

Figure 1:
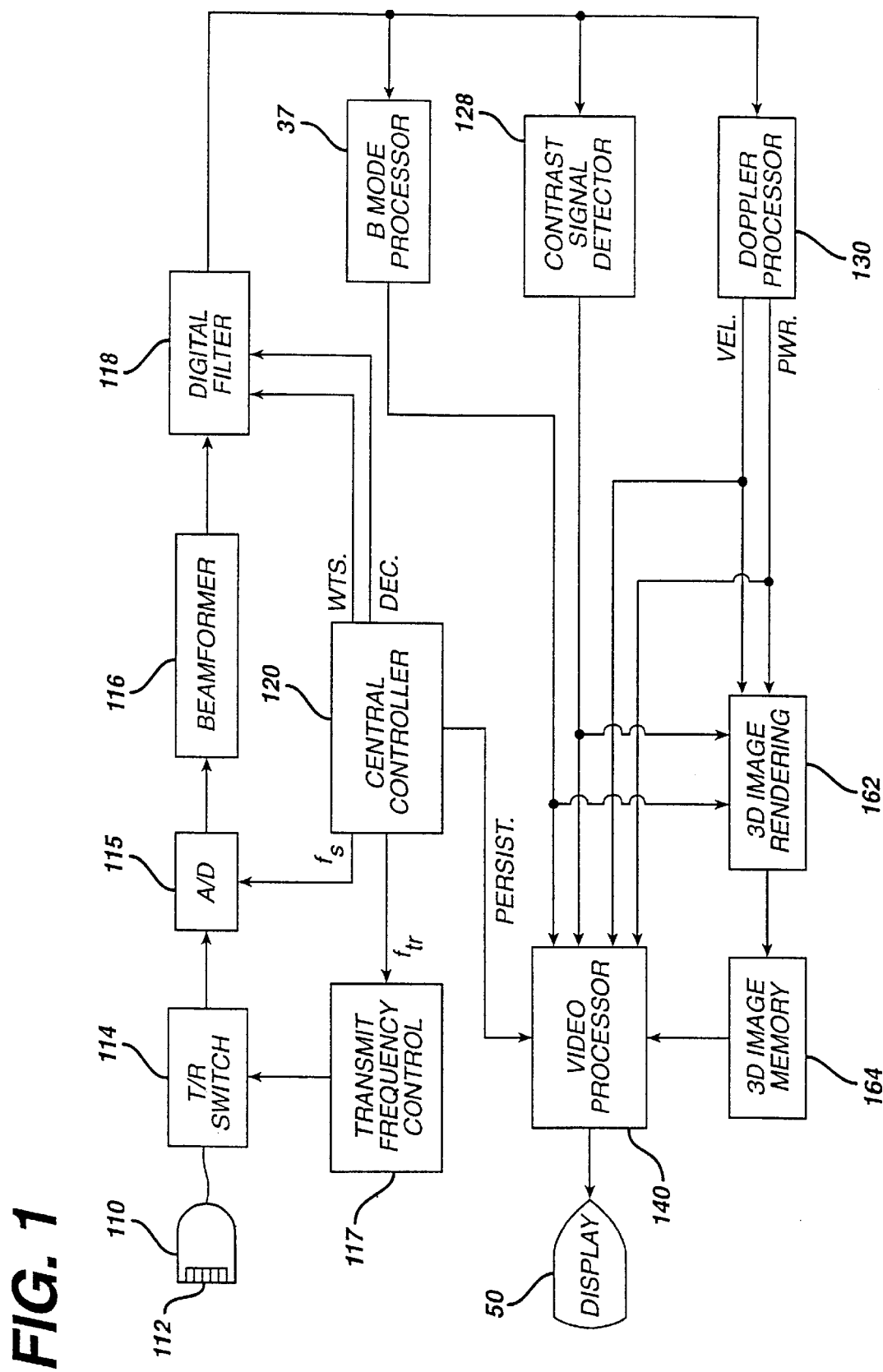

Referring first to FIG. 1, an ultrasonic diagnostic imaging system constructed in accordance with the principles of the present invention is shown in block diagram form. A central controller 120 commands a transmit frequency control 117 to transmit a desired transmit frequency band. The parameters of the transmit frequency band, $f_{tr}$, are coupled to the transmit frequency control 117, which causes the transducer 112 of ultrasonic probe 110 to transmit ultrasonic waves in the fundamental frequency band. In a constructed embodiment a band of frequencies located about a central frequency of 1.67 MHz is transmitted. This is lower than conventional transmitted imaging frequencies, which generally range from 2.5 MHz and above. However, use of a typical transmit frequency of 3 or 5 MHz will produce harmonics at 6 and 10 MHz. Since higher frequencies are more greatly attenuated by passage through the body than lower frequencies, these higher frequency harmonics will experience significant attenuation as they return to the probe. This reduces the depth of penetration and image quality at greater imaging depths, although the harmonic signals, created as they are during the propagation of the transmitted wave through tissue, do not experience the attenuation of a full round trip from the transducer as the fundamental signals do. To overcome this problem, the central transmit frequency in the illustrated embodiment is below 5 MHz, and preferably below 2.5 MHz, thereby producing lower frequency harmonics that are less susceptible to depth dependent attenuation and enabling harmonic imaging at greater depths. A transmitted fundamental frequency of 1.67 MHz will produce second harmonic return signals at 3.34 MHz in the illustrated embodiment. It will be understood, of course, that any ultrasonic frequency may be used, with due consideration of the desired depth of penetration and the sensitivity of the transducer and ultrasound system.

Figure 6:
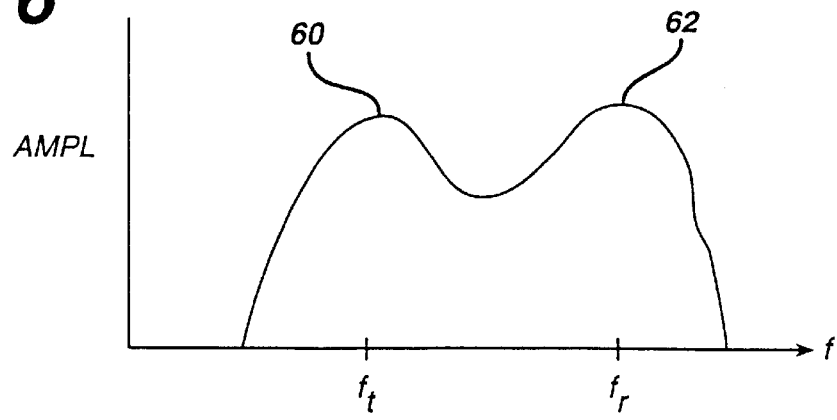
Figure 7:
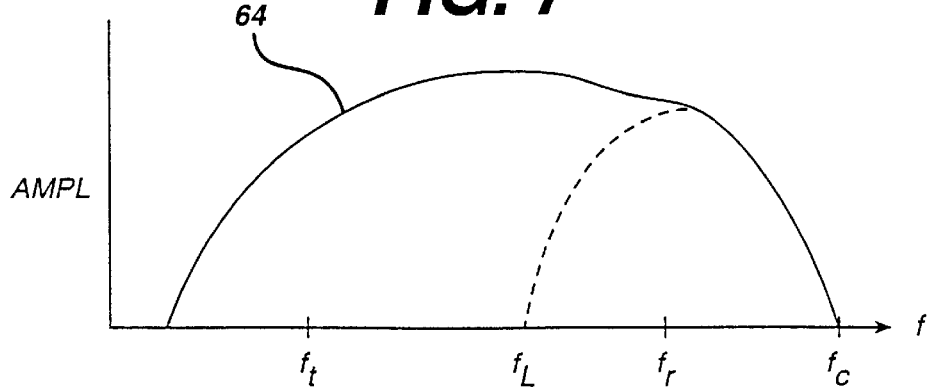

The array transducer 112 of the probe 110 transmits ultrasonic energy and receives echoes returned in response to this transmission. The response characteristic of the transducer can exhibit two passbands, one around the fundamental transmit frequency and another about a harmonic frequency in the received passband. For harmonic imaging, a broadband transducer having a passband encompassing both the transmitted fundamental and received harmonic passbands is preferred. The transducer may be manufactured and tuned to exhibit a response characteristic as shown in FIG. 6, in which the lower hump 60 of the response characteristic is centered about the transmitted fundamental frequency $f_t$, and the upper hump 62 is centered about the received harmonic frequency $f_r$ of the response passband. The transducer response characteristic of FIG. 7 is preferred, however, as the single dominant characteristic 64 allows the probe to be suitable for both harmonic imaging and conventional broadband imaging. The characteristic 64 encompasses the transmitted fundamental frequency $f_t$, and also the harmonic receive passband bounded between frequencies $f_L$ and $f_c$ and centered about frequency $f_r$. As discussed above, a low fundamental transmit frequency of 1.67 MHz will result in harmonic returning echo signals at a frequency of 3.34 MHz. A response characteristic 64 of approximately 2 MHz would be suitable for these fundamental and harmonic frequencies.

Tissue and cells in the body alter the transmitted fundamental frequency signals during propagation and the returned echoes contain harmonic components of the originally transmitted fundamental frequency. In FIG. 1 these echoes are received by the transducer array 112, coupled through the T/R switch 114 and digitized by analog to digital converters 115. The sampling frequency $f_s$ of the A/D converters 115 is controlled by the central controller. The desired sampling rate dictated by sampling theory is at least twice the highest frequency $f_c$ of the received passband and, for the preceding exemplary frequencies, might be on the order of at least 8 MHz. Sampling rates higher than the minimum requirement are also desirable.

Figure 9:
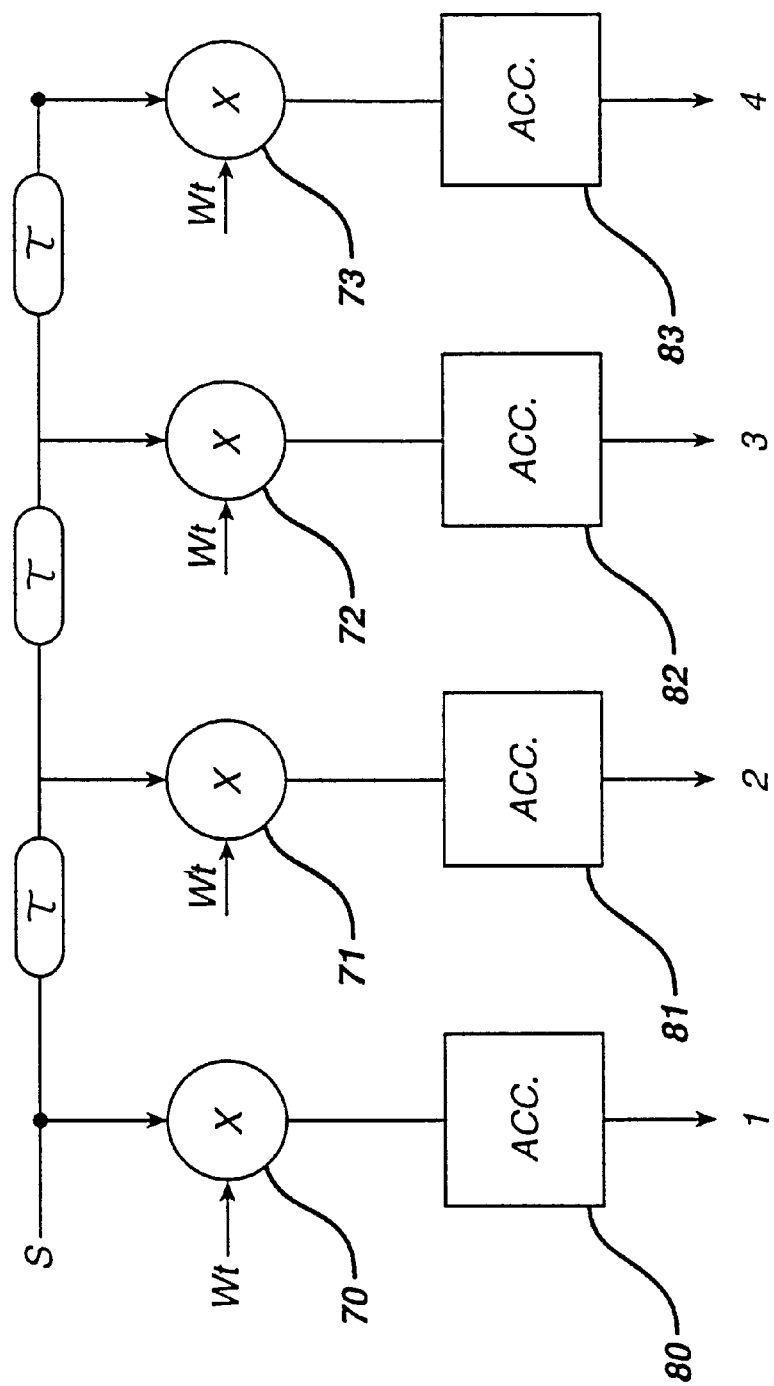
FIG. 9 illustrates an FIR filter structure suitable for use in the embodiment of FIG. 1.

The echo signal samples from the individual transducer elements are delayed and summed by a beamformer 116 to form coherent echo signals. The digital coherent echo signals are then filtered by a digital filter 118. In this embodiment, the transmit frequency $f_t$ is not tied to the receiver, and hence the receiver is free to receive a band of frequencies which is different from the transmitted band. The digital filter 118 bandpass filters the signals in the passband bounded by frequencies $f_L$ and $f_c$ in FIG. 7, and can also shift the frequency band to a lower or baseband frequency range. The digital filter could be a filter with a 1 MHz passband and a center frequency of 3.34 MHz in the above example. A preferred digital filter is a series of multipliers 70–73 and accumulators 80–83 as shown in FIG. 9. This arrangement is controlled by the central controller 120, which provides multiplier weights and decimation control which control the characteristics of the digital filter. Preferably the arrangement is controlled to operate as a finite impulse response (FIR) filter, and performs both filtering and decimation. For example, only the first stage output 1 could be controlled to operate as a four tap FIR filter with a 4:1 decimation rate. Temporally discrete echo samples S are applied to the multiplier 70 of the first stage. As the samples S are applied, they are multiplied by weights provided by the central controller 120. Each of these products is stored in the accumulator 80 until four such products have been accumulated (added). An output signal is then produced at the first stage output 1. The output signal has been filtered by a four tap FIR filter since the accumulated total comprises four weighted samples. Since the time of four samples is required to accumulate the output signal, a 4:1 decimation rate is achieved. One output signal is produced for every four input samples. The accumulator is cleared and the process repeats. It is seen that the higher the decimation rate (the longer the interval between output signals), the greater can be the effective tap number of the filter.

Alternatively, temporally separate samples are delayed by delay elements τ and applied to the four multipliers 70 73, multiplied, and accumulated in the accumulators 80–83. After each accumulator has accumulated two products, the four output signals are combined as a single output signal. This means that the filter is operating as an eight tap filter with a 2:1 decimation rate. With no decimation, the arrangement can be operated as a four tap FIR filter. The filter can also be operated by applying echo signals to all multipliers simultaneously and selectively time sequencing the weighting coefficients. A whole range of filter characteristics are possible through programming of the weighting and decimation rates of the filter, under control of the central controller. The use of a digital filter provides the advantage of being quickly and easily changed to provide a different filter characteristic. A digital filter can be programmed to pass received fundamental frequencies at one moment, and harmonic frequencies at the next. The digital filter can thus be operated to alternately produce images or lines of fundamental and harmonic digital signals, or lines of different alternating harmonics in a time-interleaved sequence simply by changing the filter coefficients during signal processing.

Returning to FIG. 1, to image just a non-fundamental frequency, the digital filter 118 is controlled by the central controller 120 to pass echo signals at a harmonic frequency for processing, to the exclusion of the fundamental frequency. The harmonic echo signals from the tissue are detected and processed by either a B mode processor 37 or a contrast signal detector 128 for display as a two dimensional ultrasonic image on the display 50.

The filtered echo signals from the digital filter 118 are also coupled to a Doppler processor 130 for conventional Doppler processing to produce velocity and power Doppler signals. The outputs of these processors are coupled to a 3D image rendering processor 162 for the rendering of three dimensional images, which are stored in a 3D image memory 164. Three dimensional rendering may be performed as described in U.S. Pat. No. 5,720,291, and in U.S. Pat. Nos. 5,474,073 and 5,485,842, the latter two patents illustrating three dimensional power Doppler ultrasonic imaging techniques. The signals from the contrast signal detector 128, the processors 37 and 130, and the three dimensional image signals are coupled to a video processor 140 where they may be selected for two or three dimensional display on an image display 50 as dictated by user selection.

It has been found that harmonic imaging of tissue and blood can reduce near field clutter in the ultrasonic image. It is believed that the harmonic response effect in tissue is dependent upon the energy level of the transmitted waves. Near to an array transducer which is focused at a greater depth, transmitted wave components are unfocused and of insufficient energy to stimulate a detectable harmonic response in the near field tissue. But as the transmitted wave continues to penetrate the body, the higher intensity energy will give rise to the harmonic effect as the wave components begin to focus. While both near and far field regions will return a fundamental frequency response, clutter from these signals is eliminated by the passband of the digital filter 118, which is set to the harmonic frequency band. The harmonic response from the tissue is then detected and displayed, while the clutter from the near field fundamental response is eliminated from the displayed image.

Figure 2:
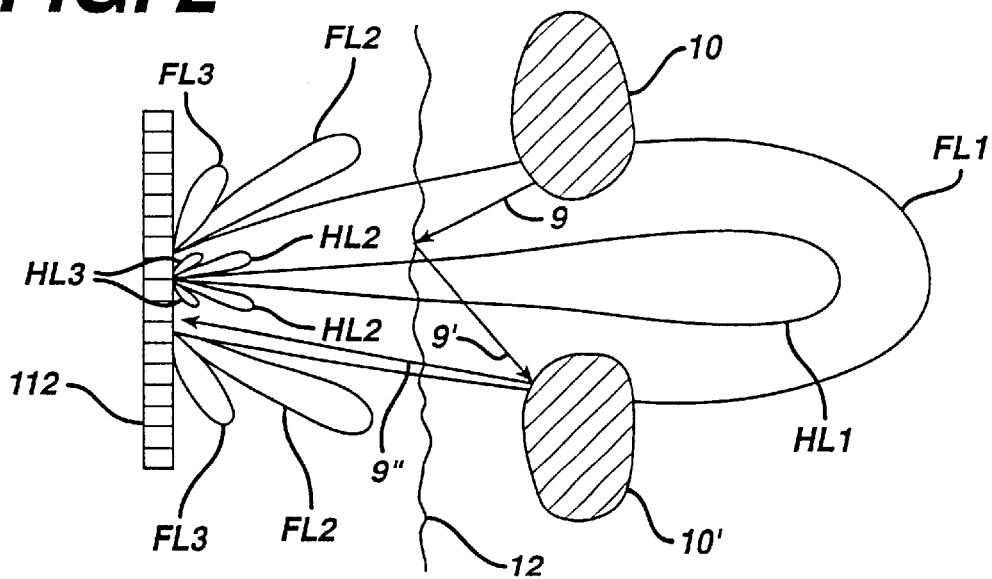

FIGS. 2, 3, 4, and 5 illustrate some of the properties of harmonic return signals which can be utilized to advantage in ultrasonic imaging. It should be appreciated that several of these properties and their interactions are not yet fully and commonly understood among the scientific community, and are still the subject of research and discussion. FIG. 2 illustrates the spatial response, and specifically the main lobe and sidelobes, of fundamental and harmonic signals received by a transducer array 112. In this illustration the array is directed to image an area of the body behind the ribs, such as the heart, and the main lobe is seen to extend between ribs 10 and 10'. Overlying the ribs is a tissue interface 12, as from a layer of fat between the skin and ribs. The FIG. shows a main lobe of the fundamental signals FL1, and on either side of the main lobe are sidelobes FL2 and FL3. The FIG. also shows the main lobe HL1 of a harmonic of the fundamental frequency, and sidelobes HL2 and HL3 of the harmonic main lobe.

In this example it is seen that the main lobe of the fundamental echoes is wide enough to encompass portions of the ribs 10,10'. Accordingly, acoustic energy at the fundamental can be reflected back toward the transducer 112 as indicated by the arrow 9. While some of the energy of this reflection may travel back to and be received directly by the transducer, in this example some of the reflected energy is reflected a second time by the tissue interface 12, as indicated by arrow 9'. This second reflection of energy reaches the other rib 10', where it is reflected a second time as shown by arrow 9" and travels back to and is received by the transducer 112.

Since the intent of this imaging procedure is to image the heart behind the ribs, these echoes reflected by the ribs are unwanted artifacts which contaminate the ultrasonic image. Unwanted echoes which are reflected a number of times before reaching the transducer, such as those following the paths of arrows 9,9',9", are referred to as multipath artifacts. Together, these artifacts are referred to as image "clutter", which clouds the near field and in some cases all of the image. This near field haze or clutter can obscure structure which may be of interest near the transducer. Moreover, the multipath artifacts can be reproduced in the image at greater depths due to the lengthy multiple paths traveled by these artifacts, and can clutter and obscure regions of interest at greater depths of field.

But when only the harmonic return signals are used to produce the ultrasonic image, this clutter from the fundamental frequencies is filtered out and eliminated. The main lobe HL1 of the received harmonic echoes is narrower than that of the fundamental, and in this example passes between the ribs 10,10' without intersecting them. There are no harmonic returns from the ribs, and no multipath artifacts from the ribs. Thus, the harmonic image will be distinctly less cluttered and hazy than the fundamental image, particularly in the near field in this example.

Figure 3:
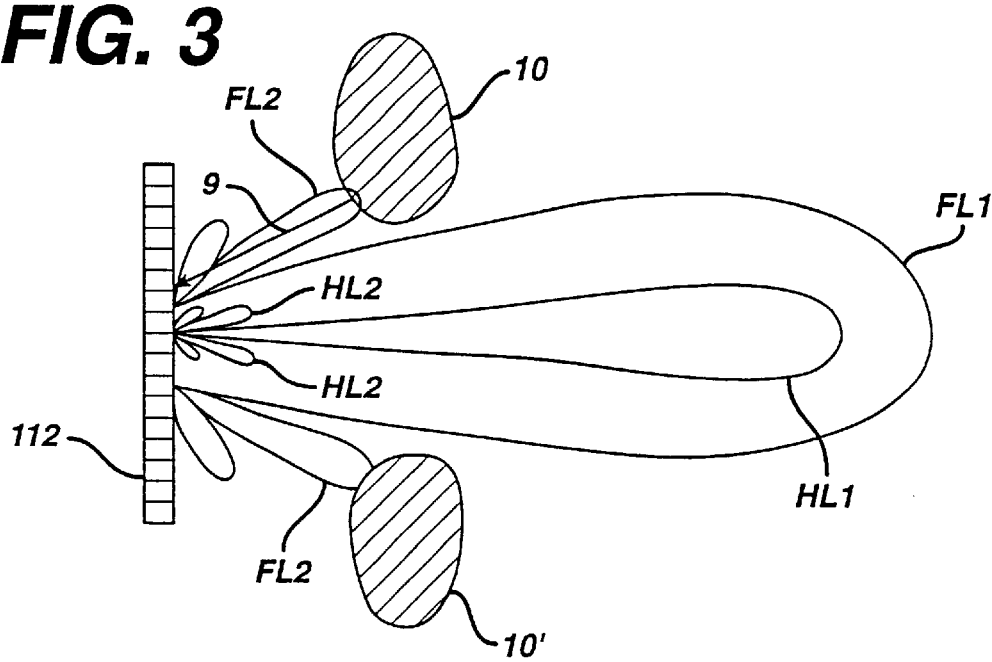

FIG. 3 shows a second example in which the main lobes of both the fundamental and harmonic returns do not intersect the ribs, and the problem discussed in FIG. 2 does not arise. But in this example the ribs 10, 10' are closer to the skin surface and the transducer 112. While the main lobes do not intersect the ribs, the sidelobes FL2 of the fundamental do reach the ribs, allowing sidelobe energy to be reflected back to the transducer as shown by reflection path 9. Again, this will produce clutter in the fundamental image. But the smaller and narrower sidelobes HL2 of the received harmonic energy do not reach the ribs. Again, the harmonic image will exhibit reduced clutter as compared to the fundamental image.

Figure 4:
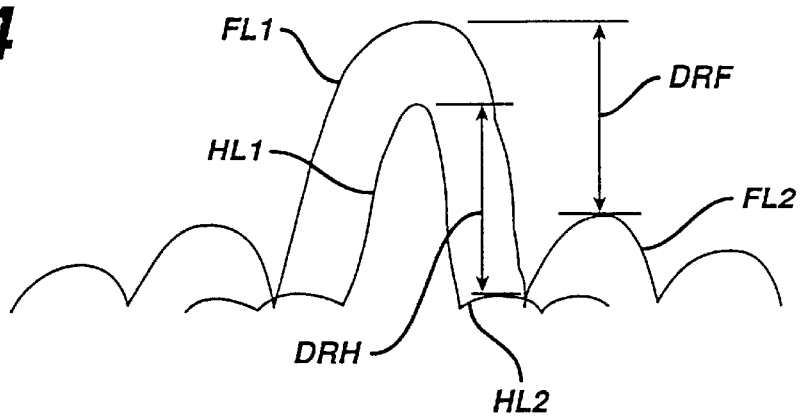

FIG. 4 illustrates the fundamental and harmonic beam patterns in a perspective which is across the lobes of FIGS. 2 and 3, that is, across the axis of the transducer. This drawing illustrates the relative amplitude responses of the fundamental and second harmonic beam patterns. Illustrated are the dynamic response DRF between the main (FL1) and first sidelobe (FL2) of the fundamental component of the sound beam, and the dynamic response DRH between the main (HL1) and first sidelobe (HL2) of the second harmonic component. If responses due to the main lobes are considered desired signal responses, and responses due to the sidelobes are considered to be clutter or noise, the signal to noise ratio of the harmonic is greater than that of the fundamental. That is, there is relatively less sidelobe clutter in a harmonic image than in the corresponding fundamental image of the same transmission, or DRH> DRF.

Figure 5:
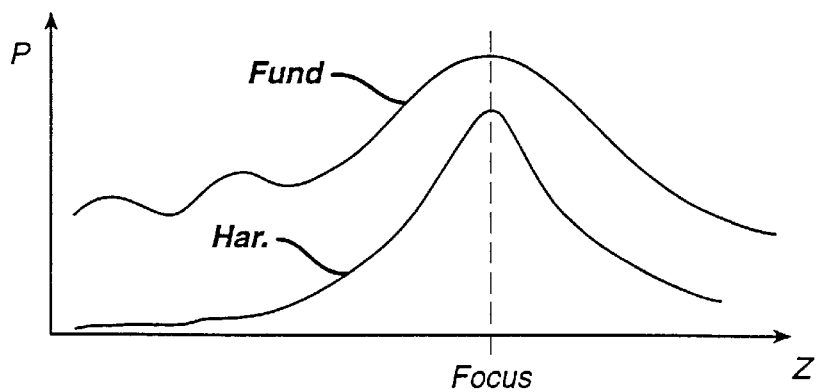

FIG. 5 illustrates another comparison of the properties of fundamental and harmonic signals, which is the relative amount of energy (in units of acoustic pressure P) emanating from increasing depths Z in the body at the fundamental and second harmonic frequencies. The curve denoted Fund. shows the buildup of propagated acoustic energy at the fundamental frequency. While the curve is seen to peak at the focus of the array transducer, it is seen that there is nonetheless an appreciable amount of fundamental energy at the shallower depths before the focal region. In comparison, there is comparatively much less energy, and a lesser buildup of energy, at the harmonic frequency propagated at these lesser depths of field. Hence, with less energy available for multipath reverberation and other aberrations, there is less near field clutter with harmonic imaging than with imaging the fundamental echo returns from the same transmission.

Figure 8:
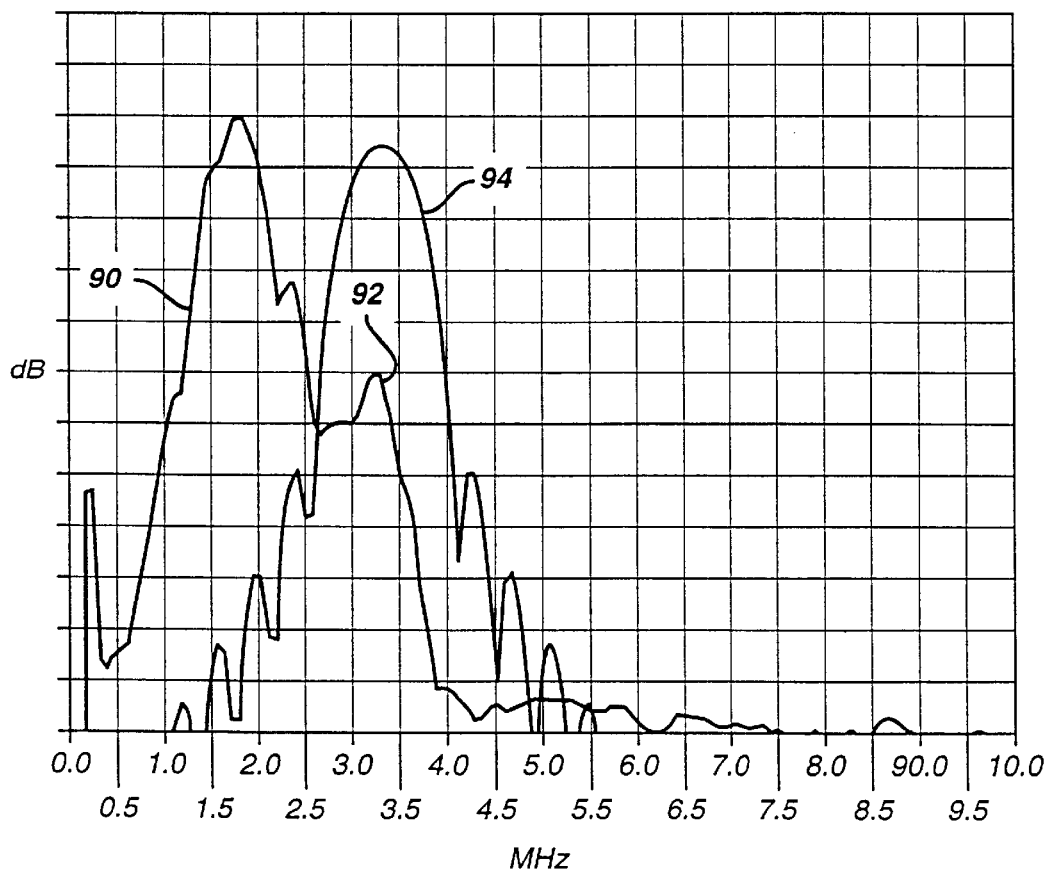
FIG. 8 illustrates typical fundamental and harmonic frequency passbands of an embodiment of the present invention.

FIG. 8 illustrates the bands of received signals and the digital filter of a typical FIG. 1 embodiment of the present invention for a transmitted signal of four cycles of a 1.67 MHz acoustic wave. Transmitting multiple cycles narrows the bandwidth of the transmitted signal; the greater the number of cycles, the narrower the bandwidth. In response to this transmission, the transducer 112 receives a fundamental signal in a bandwidth 90, which is seen to peak at the transmitted frequency of 1.67 MHz. As the fundamental frequency band rolls off, the harmonic band 92 comes up, and is seen to exhibit a peak return at the harmonic frequency of 3.34 MHz. The received signals are applied to a digital filter with a passband characteristic 94, which is seen to be centered around the harmonic frequency of 3.34 MHz. As FIG. 8 shows, this passband will substantially suppress signals at the fundamental frequency while passing the harmonic signals on to further processing and image formation. When imaging the heart in this manner, it has been found that the harmonic response of the endocardial tissue of the heart is quite substantial, and harmonic tissue images of the heart show a clearly defined endocardial border.

Other signal processing techniques besides filtering may be used to separate out harmonic signals from received echo information such as cancellation of the fundamental frequencies in a broadband signal, leaving only the harmonic frequencies. For example, U.S. Pat. No. 5,706,819 discloses a two pulse technique, whereby each scanline is insonified by consecutive fundamental frequency pulses of opposite phase in rapid succession. When the resultant echoes are received from the two pulses and combined on a spatial basis, the fundamental frequencies will cancel and the nonlinear or harmonic frequencies will remain. Thus, the harmonic frequencies are separated from the broadband echo signals without the need for a filter circuit.

Figure 10:
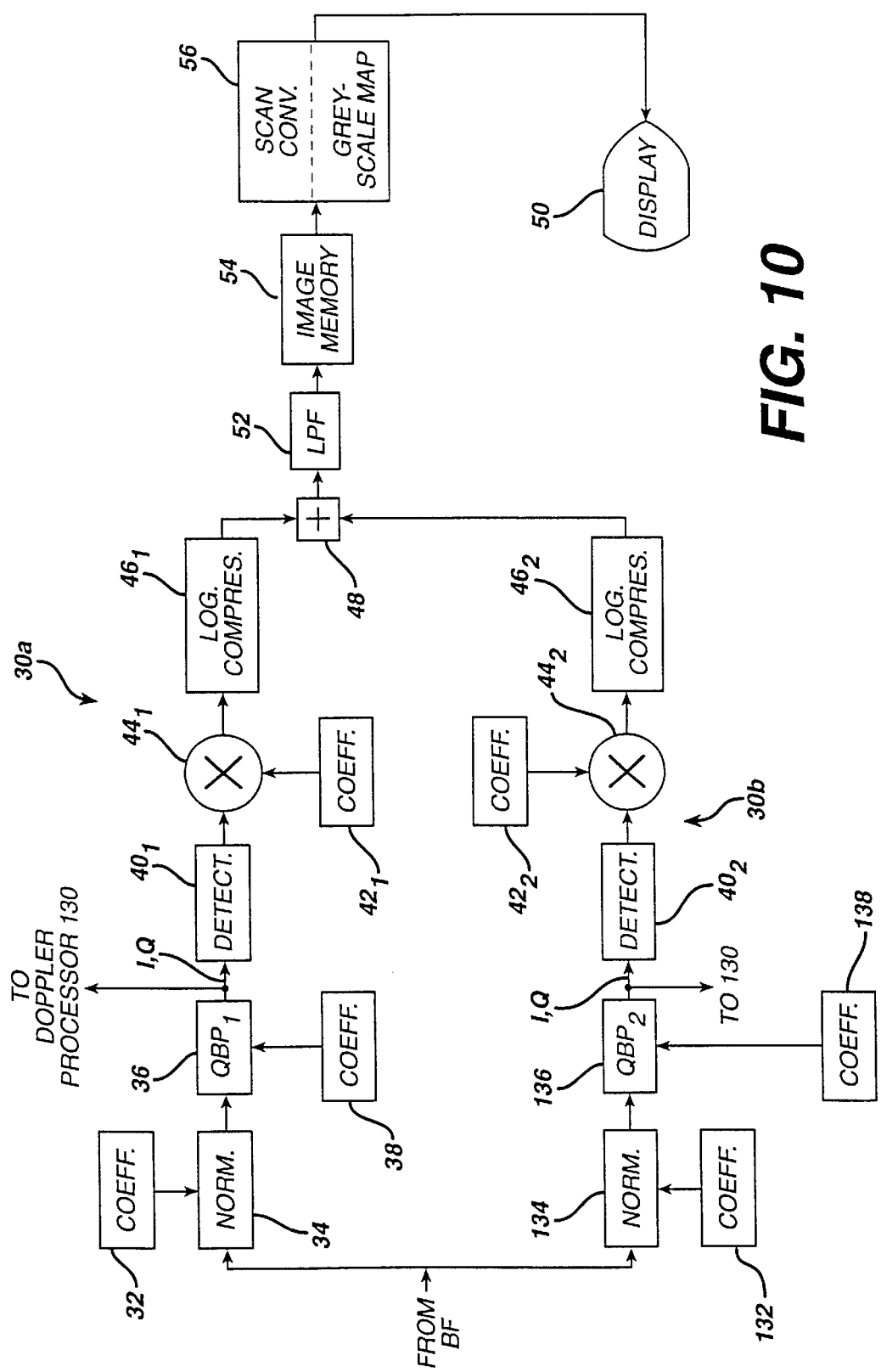
FIG. 10 illustrates in block diagram form a portion of a preferred embodiment of the present invention.

FIG. 10 shows a portion of a preferred embodiment of the present invention in block diagram form, from the beamformer output through to the image display. This embodiment not only produces harmonic images of tissue and blood flow, but also overcomes signal dropout deficiencies of conventional imaging systems which arise when imaging patients with difficult to image pathology. Additionally, this embodiment reduces an artifact of coherent ultrasound images known as speckle. In FIG. 10, the signal and data lines connecting the blocks of the block diagram all represent multi-conductor digital data paths, as the processor of the illustrated embodiment is entirely digital. Scanline echo data from the beamformer 116 is applied in parallel to the two channels 30a,30b of the processor illustrated in FIG. 10, one of which is a high frequency channel and the other of which is a low frequency channel. Each channel of the processor has a normalization stage 32,132 which multiplies the scanline data by a scale factor on a sample by sample basis to produce gain or attenuation that can vary with the depth of the body from which each sample returned. The scale factor for each channel is provided by normalization coefficients stored in or generated by coefficient circuits 32,132, which in a preferred embodiment are digital memories. As the multiplying coefficients are changed along the sequence of scanline echoes, depth dependent gain or attenuation is produced.

The function of the normalization stages is two-fold. One is to compensate for a transducer aperture which expands with depth of scan. As signals from an increasing number of transducers are used with increasing depth, the magnitude of the summed beamformed signals will increase. This increase is offset by reduced gain (increased attenuation) in the normalization stage, in proportion to the rate at which channels are added to the beamforming process, so that the resultant echo sequence will be unaffected by the changing aperture.

Figure 11:
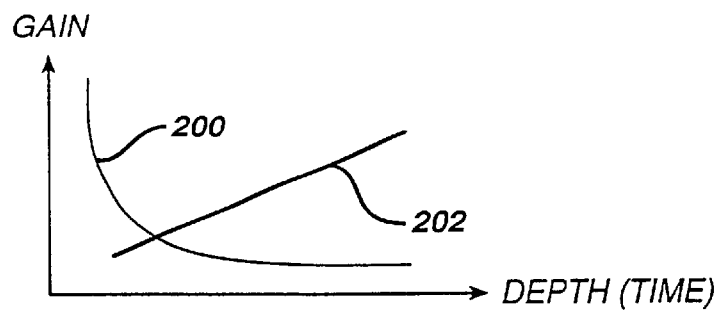
FIG. 11 illustrates the operation of the normalization stages of the embodiment of FIG. 10.

The second function of the normalization stages is to equalize the nominal signal amplitudes of the two channels 30a,30b. The nominal signal amplitudes of the passbands of the two channels are desirably the same, so that the original relative signal levels will be preserved after the passbands are summed to create the full harmonic passband. But ultrasound signals are subject to depth dependent attenuation which varies with frequency, higher frequencies being more greatly attenuated with depth than lower frequencies. To account for this depth dependent attenuation the coefficients for the normalization stages provide signal gain which increases with depth. Since the two channels employ different frequency passbands, the depth dependent gain of the two channels differs from one channel to the other. In particular, the rate of gain increase for the higher frequency passband channel is greater than that of the lower frequency passband channel. This is illustrated in FIG. 11, which, for purposes of illustration, shows the normalization gain characteristic of the higher frequency passband channel separated into two components. The depth dependent characteristic 200 offsets the effect of an increasing aperture in the channel, and the depth dependent characteristic 202 compensates for depth dependent signal attenuation. The low frequency passband channel may also have a depth dependent gain characteristic but with a different characteristic 202 for the different rate of attenuation of the lower frequencies. The high frequency passband channel has a similar but more rapidly increasing depth dependent gain characteristic to account for the more rapid rate of attenuation of the higher frequencies. Each depth dependent gain characteristic 202 is chosen to offset the effect of depth dependent gain for the particular frequency passband employed by that channel.

In a preferred embodiment the coefficients of the coefficient circuits apply a gain or attenuation characteristic which is a combination of the two characteristics 200,202. Preferably, the coefficient memories 32,132 store multiple combined gain curves which are changed with memory addressing to match scanhead characteristics or the type of signals being processed (2D or Doppler). The rate of gain change may be controlled by the rate at which the coefficients are changed for the multiplier of each normalization stage 30,130.

Figure 12:
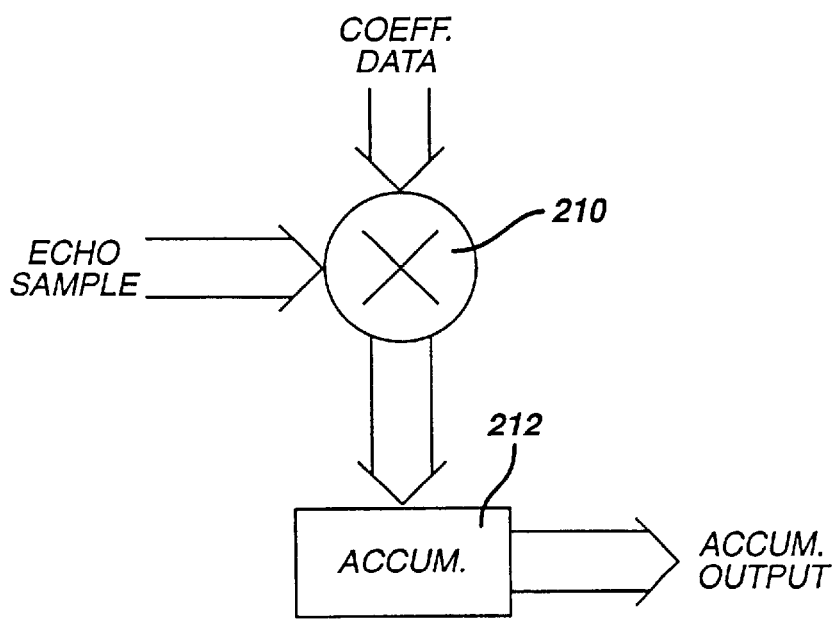
FIG. 12 is a block diagram of one of the multiplier accumulators used in the filters of the embodiment of FIG. 10.

The normalized echo signals in each channel are coupled to quadrature bandpass filters (QBPs) in each channel. The quadrature bandpass filters provide three functions: band limiting the RF scanline data, producing in-phase and quadrature pairs of scanline data, and decimating the digital sample rate. Each QBP comprises two separate filters, one producing in-phase samples (I) and the other producing quadrature samples (Q), with each filter being formed by a plurality of multiplier-accumulators (MACs) implementing an FIR filter. One such MAC is shown in FIG. 12. As an echo sample of the scanline data is applied to one input of a digital multiplier 210 a coefficient is applied to the other multiplier input. The product of the echo sample and the weighting coefficient is stored in an accumulator 212 where it may be accumulated with previous products. Other MACs receive the echo samples at different phases and likewise accumulate weighted echo samples. The accumulated outputs of several MACs can be combined, and the final accumulated product comprises filtered echo data. The rate at which accumulated outputs are taken sets the decimation rate of the filter. The length of the filter is a product of the decimation rate and the number of MACs used to form the filter, which determine the number of incoming echo samples used to produce the accumulated output signal. The filter characteristic is determined by the values of the multiplying coefficients. Different sets of coefficients for different filter functions are stored in coefficient memories 38,138, which are coupled to apply selected coefficients to the multipliers of the MACs. The MACs effectively convolve the received echo signals with sine and cosine representative coefficients, producing output samples which are in a quadrature relationship.

The coefficients for the MACs which form the I filter implement a sine function, while the coefficients for the Q filter implement a cosine function. For bandpass filtering, the coefficients of the active QBPs additionally implement a low pass filter function that is frequency shifted to form, in combination with the sine (for I) and cosine (for Q) functions, a bandpass filter for the quadrature samples. In the instant example, $QBP_1$ in channel 30a is producing I and Q samples of the scanline data in a first, low frequency passband, and $QBP_2$ in channel 30b is producing I and Q samples of the scanline data in a second, higher frequency passband. Thus, the spectrum of the original broadband echo signals is divided into a high frequency band and a low frequency band. To complete the dropout and speckle reduction process, the echo data in the passband produced by $QBP_1$ of channel 30a is detected by a detector $40_1$ and the detected signals are coupled to one input of a summer 48. In a preferred embodiment detection is performed digitally by implementing the algorithm $(I^2+Q^2)^{1/2}$. The echo data in the complementary passband produced by $QBP_2$ of channel 30b is detected by a detector 402 and these detected signals are coupled to a second input of the summer 48. When the signals of the two passbands are combined by the summer 48, the decorrelated signal dropout and speckle effects of the two passbands will at least partially cancel, reducing the signal dropout and speckle artifacts in the 2D image created from the signals.

Following the detector in each subchannel is a gain stage formed by multipliers $44_1,44_2$ which receive weighting coefficients from coefficient memories $42_1,42_2$. The purpose of this gain stage is to partition the balance of analog and digital gains in the ultrasound system for optimal system performance. Some of the gains in the echo signal path may be automatically implemented by the ultrasound system, while others, such as manual gain control and TGC gain, may be controlled by the user. The system partitions these gains so that the analog gains preceding the ADCs (analog to digital converters) of the beamformer are adjusted optimally for the dynamic input range of the ADCs. The digital gain is adjusted to optimize the brightness of the image. The two gains together implement gain control changes effected by the user.

In the preferred embodiment the gain imparted to the scanline signals by the multipliers $44_1,44_2$ is selected in concert with the gain of the preceding normalization stage 34,134 in the channel. The gain of each normalization stage is chosen to prevent the attainment of saturation levels in the QBPs, as may occur when strong signals from contrast agents or harmonic imaging are being received. To prevent saturation levels the maximum gain of the normalization stage is controlled, and any reduction imposed by reason of this control is restored by the gain of the succeeding multiplier $44_1,44_2$.

The gain function provided by these multipliers could be performed anywhere along the digital signal processing path. It could be implemented by changing the slope of the compression curves discussed below. It could also, for instance, be performed in conjunction with the gains applied by the normalization stages. This latter implementation, however, would eliminate the ability to effect the saturation control discussed above. The present inventors have found implementation of this gain function to be eased when provided after detection, and in the preferred embodiment by use of a multiplier after detection.

The signals produced by the gain stages $44_1,44_2$ generally exhibit a greater dynamic range than may be accommodated by the display 50. Consequently, the scanline signals of the multipliers are compressed to a suitable dynamic range by lookup tables. Generally compression is logarithmic, as indicated by log compression processors $46_1,46_2$. The output of each lookup table is proportional to the log of the signal input value. These lookup table are programmable so as to provide the ability to vary the compression curves, and the brightness and dynamic range of the scanline signals sent on for display.

Figure 13:
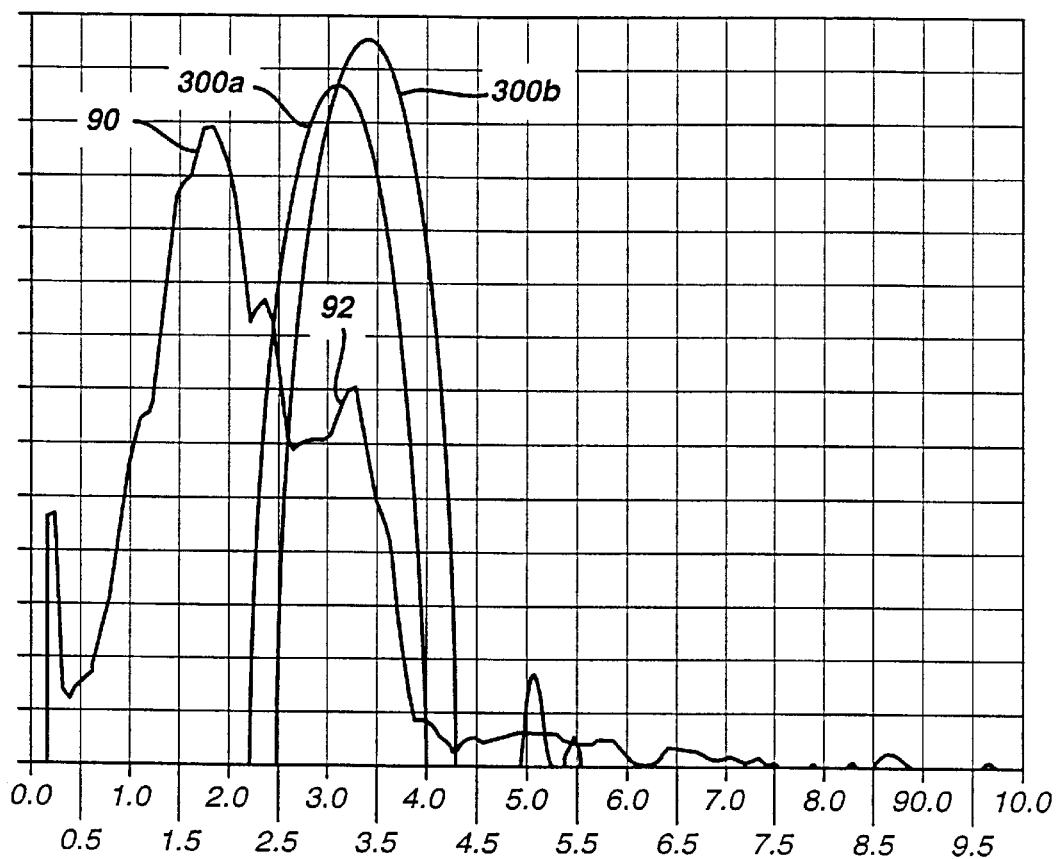
FIG. 13 illustrates typical fundamental and harmonic frequency passbands of the embodiment of FIG. 10.

The present inventors have found that the use of log compression to scale the echo signals can affect low level signals near the baseline (black) level of the signal dynamic range by exacerbating the degree and the number of echoes with components at the black level, a manifestation of the destructive interference arising from the speckle effect of the coherent ultrasonic energy. When the echo signals are displayed, many of them will be at the black level, and appear in the image to have been undetected or dropped out. The embodiment of FIG. 10 reduces this problem by producing separate, partially decorrelated versions of the echo signals in the two channels 30a,30b. This embodiment partially decorrelates the echo signal versions by separating the echo signal components into two different passbands as shown in FIG. 13. The two passbands can be completely separated or, as shown in this example, overlapping. In this example, the lower passband 300a is centered about a frequency of 3.1 MHz, and the higher passband 300b is centered about a frequency of 3.3 MHz, a center frequency separation of only 200 kHz. Even this small degree of separation has been found sufficient to decorrelate the signal components of the two passbands sufficiently such that black level signal dropout in one passband will frequently not align in frequency with its corresponding component in the other passband. Consequently, when these decorrelated replicas of the same echo signal are combined by the summer 48, the signal dropout and speckle artifacts will be markedly reduced. This is especially significant when trying to image fine structures at deep depths in the body, such as the endocardium. A harmonic image of the endocardium is significantly improved by the artifact elimination effects of the embodiment of FIG. 10.

As discussed previously the signal gain of the two passbands 300a,300b of FIG. 13 can be matched to preserve the original signal levels after summation. However, in a preferred embodiment, the lower frequency passband is processed with less dynamic range than the higher frequency passband as shown in FIG. 13. This has the effect of suppressing the fundamental frequency contributions of the lower frequency passband (which contains more fundamental frequency components than the higher frequency band.) This is accomplished as a component of different compression characteristics in the log compression processors $46_1$, $46_2$, or elsewhere in the channels 30a,30b subsequent to the separation of the broadband signal into separate passbands.

The processed echo signals at the output of the summer 48 are coupled to a lowpass filter 52. This lowpass filter, like the QBPs, is formed by combinations of multiplier-accumulators with variable coefficients, arranged to implement an FIR filter, to control the filter characteristic. The lowpass filter provides two functions. One is to eliminate sampling frequency and other unwanted high frequency components from the processed echo signals. A second function is to match the scanline data rate to the vertical line density of the display 50, so as to prevent aliasing in the displayed image. The FIR filter performs this function by selectively decimating or interpolating the scanline data. The filtered echo signals are then stored in an image memory 54. If the scanlines have not yet been scan converted, that is, they have r,θ coordinates, the scanlines are scan converted to rectilinear coordinates by a scan converter and greyscale mapping processor 56. If scan conversion has been performed earlier in the process, or is not needed for the image data, the processor 56 may simply convert the echo data to the desired greyscale map by a lookup table process. The image data may then be stored in a final image memory or sent to a video display driver (not shown) for conversion to display signals suitable for driving the display 50.

It will be appreciated that, due to the advantage of the quick programmability of a digital filter, the processing described above can be performed in an embodiment which utilizes a single one of the channels 30a, 30b to process the echo data from a scanline twice to alternately produce a line of signals for each of the two passbands in a time-interleaved fashion. However, the use of two parallel channels affords twice the processing speed, enabling harmonic images to be produced in real time and at twice the frame rate of a time multiplexed embodiment.

Figure 14:
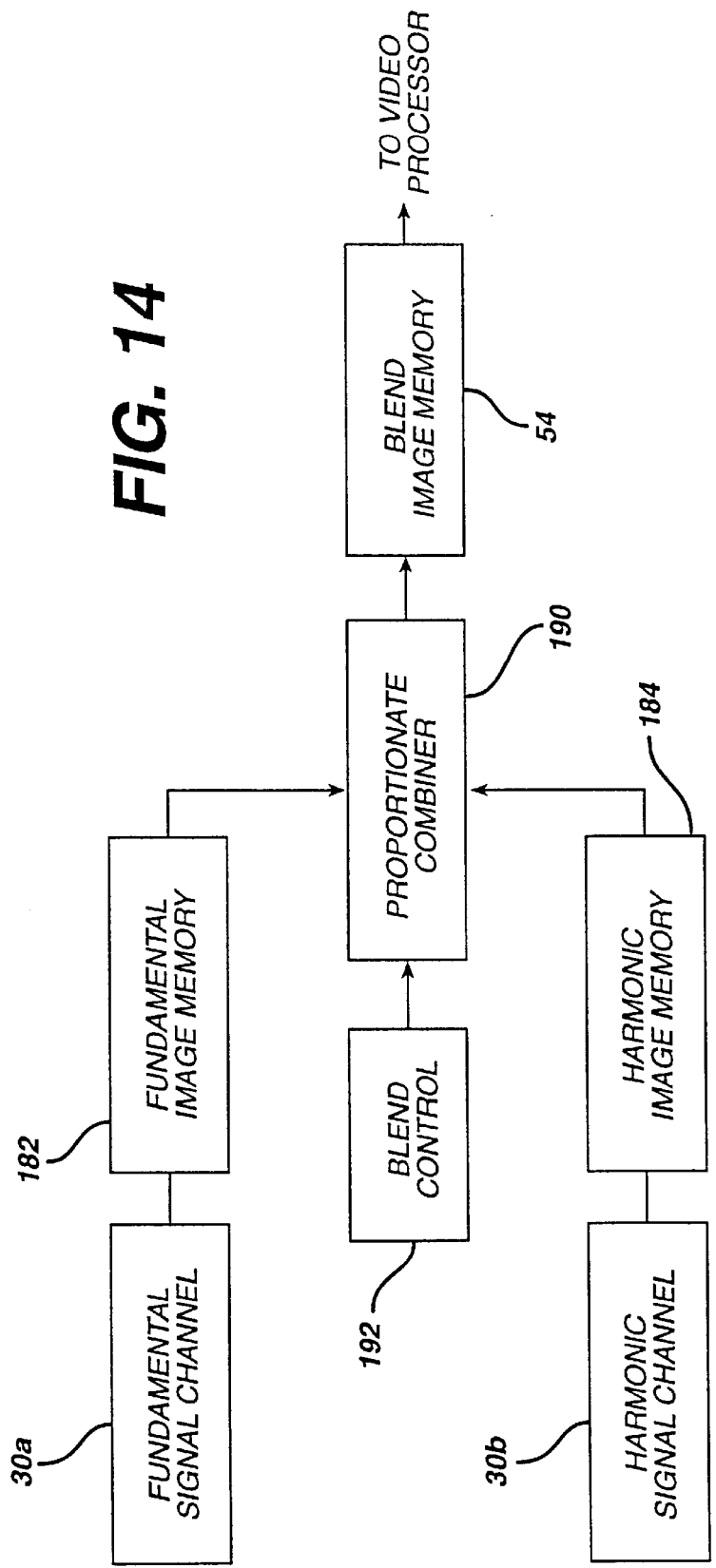
FIG. 14 illustrates the blending of fundamental and harmonic signal components into one ultrasonic image.

Harmonic images produced from high frequency signals can suffer from depth dependent attenuation as the echo signals return from increasing depths in the body. Lower frequency fundamental signals may experience less attenuation, and hence in some cases may exhibit better signal to noise ratios at greater depths. The embodiment of FIG. 14 takes advantage of this characteristic by blending fundamental and harmonic image data in one image. It is possible, for instance, to create a normal tissue image of the heart from fundamental frequencies, and overlay the fundamental frequency tissue image with a harmonic tissue image of the heart to better define the endocardial border in the composite image. The two images, one from fundamental frequency components and another from harmonic frequency components, may be formed by alternately switching the digital filter 118 between fundamental and harmonic frequencies to separately assemble fundamental and harmonic images, or by employing the two parallel filters of FIG. 10 with two passbands, one set to pass fundamental frequencies and the other set to pass harmonic frequencies. In FIG. 14, the filter of channel 30a is set to pass fundamental signal frequencies, and echo signals passed by this channel are stored in a fundamental image memory 182. Correspondingly, harmonic signal frequencies are passed by channel 30b and stored in a harmonic image memory. The fundamental and harmonic images are then blended together by a proportionate combiner 190, under control of a blend control 192. The blend control 192 may automatically implement a pre-programmed blending algorithm, or one directed by the user. For example, the proportionate combiner 190 may create a blended image which uses only echo data from the harmonic image at shallow depths, then combines echo data from both images at intermediate depths, and finally only uses echo data of the fundamental image at deep depths. This combines the reduced clutter benefit of harmonic echo data at shallow depths and the greater penetration and signal to noise ratio of fundamental echoes received from deeper depths, while affording a smooth transition from one type of data to the other at intermediate depths. Other combining algorithms are also possible, such as simply switching from one type of data to another at a predetermined depth, or outlining a region of the image to be displayed with one type of data while the remainder of the image is displayed using the other type of data.

It is also possible to employ the two parallel filters and blend the components together before image formation, thereby adding a controllable component of the harmonic echo signals to the fundamental frequency signals to enhance the resultant image. Such an embodiment could eliminate the need for separate fundamental and harmonic image memories and would process the signal components directly to a blended image memory.

Figure 15:
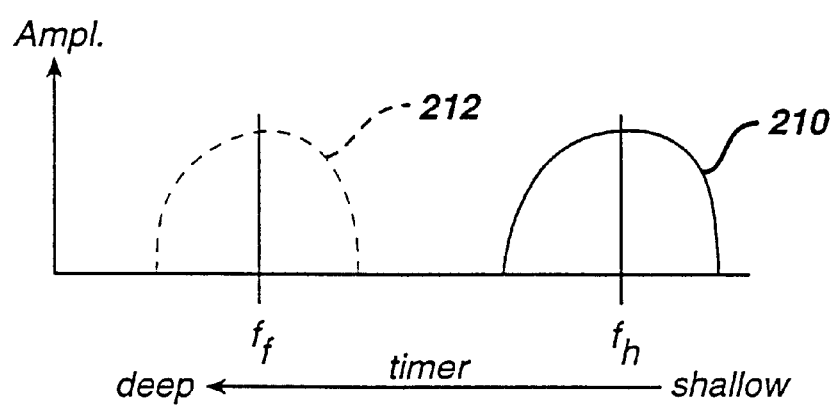
FIG. 15 illustrates the passbands of a time varying filter used in the formation of blended images.

A third technique for producing blended images is to receive each scanline of the image through a depth-dependent, time varying filter. Such filters are well known for improving the signal to noise ratio of received echo signals in the presence of depth dependent attenuation as shown, for instance, in U.S. Pat. No. 4,016,750. For the production of blended fundamental and harmonic images, the passband 210 of a time varying filter is initially set to pass harmonic frequencies $f_h$, as shown in FIG. 15, as echo signals begin to be received from shallow depths. When it becomes desirable to begin supplementing the image with fundamental signal components at deeper depths, the passband 210 undergoes a transition to lower frequencies, eventually moving to the fundamental frequencies ff as shown by passband 212 in FIG. 15. In the case of a digital filter such as that shown in FIG. 9, the change in passband frequencies is effected by changing the filter coefficients with time. As the filter undergoes this transition, the passband passes fewer harmonic frequencies and greater fundamental frequencies until eventually, if desired, the passband is passing only fundamental frequencies at the maximum image depth. By receiving each scanline through such a time varying filter, each line in the resultant image can comprise harmonic frequencies in the near field (shallow depths), fundamental frequencies in the far field (deepest depths), and a blend of the two in between.

Harmonic tissue images of moving tissue can also be formed by processing the received harmonic tissue echo signals with the processor described in U.S. Pat. No. 5,718,229, entitled MEDICAL ULTRASONIC POWER MOTION IMAGING.

Thus, the present invention encompasses an ultrasonic imaging system for imaging the nonlinear response of tissue and fluids of the body to ultrasound by transmitting a fundamental frequency signal, receiving an echo signal from the tissue at a non-fundamental, preferably harmonic, frequency, detecting the non-fundamental frequency echo signals, and forming an image of the tissue and fluids from the non-fundamental frequency echo signals. As used herein the term harmonic also refers to harmonic frequencies of higher order than the second harmonic and to subharmonics, as the principles described herein are equally applicable to higher order and subharmonic frequencies.

What is claimed is:

1. An ultrasonic diagnostic imaging system for producing a blended harmonic ultrasonic image of tissue inside a body, comprising:

means for transmitting ultrasonic energy into the body at a fundamental frequency;

means, responsive to said transmitted ultrasonic energy, for receiving ultrasonic echo signals from tissue at a plurality of depths in the body;

means for separating said echo signals into fundamental and harmonic frequency components; and an image processor which produces image signals which are a blend of proportions of said fundamental and harmonic frequency components, said proportions being predetermined to vary with echo signal depth.

2. An ultrasonic diagnostic imaging system for producing a blended harmonic ultrasonic image of tissue inside a body, comprising:

means for transmitting ultrasonic energy into the body at a fundamental frequency;

means, responsive to said transmitted ultrasonic energy, for receiving ultrasonic echo signals from tissue at a plurality of depths in the body;

means for separating said echo signals into fundamental and harmonic frequency components; and an image processor which produces image signals which are a blend of proportions of said fundamental and harmonic frequency components, said proportions varying with echo signal depth, wherein said image processor comprises means for producing image signals of predominately harmonic frequency components in the near field of an image, and image signals of predominately fundamental frequency components in the far field of an image.

3. The ultrasonic diagnostic imaging system of claim 2, wherein said image processor further comprises means for producing image signals of both harmonic and fundamental frequency components in the intermediate field between said near and far fields.

4. The ultrasonic diagnostic imaging system of claim 1, wherein said separating means includes a filter for producing fundamental frequency echo signal components to the at least partial exclusion of harmonic frequency components, and for producing harmonic frequency echo signal components to the at least partial exclusion of fundamental frequency components.

5. An ultrasonic diagnostic imaging system for producing a blended harmonic ultrasonic image of tissue inside a body, comprising:

means for transmitting ultrasonic energy into the body at a fundamental frequency;

means, responsive to said transmitted ultrasonic energy, for receiving ultrasonic echo signals from tissue at a plurality of depths in the body;

means for separating said echo signals into fundamental and harmonic frequency components; and an image processor which produces image signals which are a blend of proportions of said fundamental and harmonic frequency components, said proportions varying with echo signal depth, wherein said separating means includes a filter for producing fundamental frequency echo signal components to the at least partial exclusion of harmonic frequency components, and for producing harmonic frequency echo signal components to the at least partial exclusion of fundamental frequency components, wherein said transmitting means comprises means for transmitting two differently phased pulses of ultrasonic energy to a common region of the body, and wherein said filter combines ultrasonic echoes from said two transmitted waves to produce at least one of said fundamental and harmonic frequency echo components.

6. An ultrasonic diagnostic imaging system for producing a blended harmonic ultrasonic image of tissue inside a body, comprising:

means for transmitting ultrasonic energy into the body at a fundamental frequency;

means, responsive to said transmitted ultrasonic energy, for receiving ultrasonic echo signals from tissue at a plurality of depths in the body;

means for separating said echo signals into fundamental and harmonic frequency components; and an image processor which produces image signals which are a blend of proportions of said fundamental and harmonic frequency components, said proportions varying with echo signal depth, wherein said image processor comprises means for producing a fundamental image from said fundamental frequency components and a harmonic image from said harmonic frequency components, wherein said image processor produces a blended image which is a combination of image signals from said fundamental and harmonic images.

7. An ultrasonic diagnostic imaging system for producing a blended harmonic ultrasonic image of tissue inside a body, comprising:

a transducer for receiving ultrasonic echoes from tissue in an image area of the body in the absence of an ultrasonic contrast agent, said ultrasonic echoes containing fundamental and harmonic frequency components; and an image processor, responsive to said ultrasonic echoes, for producing an image of said image area which is a variable blend of fundamental and harmonic frequency information.

8. The ultrasonic diagnostic imaging system of claim 7, wherein said image contains a first image area region formed principally from harmonic frequency components and a second image area region formed principally from fundamental frequency components.

9. The ultrasonic diagnostic imaging system of claim 8, wherein said first image area is in the near field of said image and said second image area is in the far field of said image.

10. The ultrasonic diagnostic imaging system of claim 9, further comprising a third image area formed from a blend of both fundamental and harmonic frequency components.

11. The ultrasonic diagnostic imaging system of claim 7, wherein said blend is a function of the depth from which said ultrasonic echoes are received.

12. The ultrasonic diagnostic imaging system of claim 7, wherein said blend is a function of the location in said image area from which said ultrasonic echoes are received.

13. A method for producing an ultrasonic image which is a blend of fundamental and harmonic frequency echo information comprising the steps of:

receiving ultrasonic echoes from tissue of the body in the absence of an ultrasonic contrast agent which contain both fundamental and harmonic frequency components;

separately detecting said fundamental and harmonic frequency components of said ultrasonic echoes;

forming signals which are a blend of said detected fundamental and harmonic frequency components prior to image formation;

storing said signals in a blended image memory; and displaying an image from the signals stored in said blended image memory.

14. The method of claim 13, wherein said blend of fundamental and harmonic frequency components varies as a function of time.

15. The method of claim 13, wherein said blend of fundamental and harmonic frequency components varies as a function of depth.

16. The method of claim 13, wherein said blend of fundamental and harmonic frequency components varies as a function of the location of said tissue.

17. An ultrasonic diagnostic imaging system for producing a blended harmonic ultrasonic image of tissue inside a body, comprising:

a transducer for receiving ultrasonic echoes from tissue in an image area of the body, said ultrasonic echoes containing fundamental and harmonic frequency components;

a time varying filter, responsive to said received ultrasonic echoes, for producing signals containing different proportions of fundamental and harmonic frequency echo components at different times; and an image processor, responsive to said signals produced by said time varying filter, for producing an image which is a blend of fundamental and harmonic frequency information.

18. The ultrasonic diagnostic imaging system of claim 17, wherein said time varying filter exhibits a passband which varies from high to low frequencies over time.

19. The ultrasonic diagnostic imaging system of claim 18, wherein said time varying filter produces signals containing a relatively high proportion of harmonic frequency components from echoes received at shallow depths, and a relatively high proportion of fundamental frequency components from echoes received at deeper depths.

20. The ultrasonic diagnostic imaging system of claim 17, wherein said time varying filter comprises a digital filter.

21. The ultrasonic diagnostic imaging system of claim 20, wherein the passband of said digital time varying filter is changed by changing the filter coefficients with time.

22. An ultrasonic diagnostic imaging system for producing a harmonic ultrasonic image of tissue inside a body, comprising:

a transducer for receiving ultrasonic echoes from tissue in an image area of the body, said ultrasonic echoes containing fundamental and harmonic frequency components;

a processing channel, and responsive to said received ultrasonic echoes, which alternately produces fundamental and harmonic frequency signals in a time interleaved fashion; and an image processor, responsive to said time interleaved signals, which produces an ultrasonic image containing both fundamental and harmonic frequency signal information.

23. The ultrasonic diagnostic imaging system of claim 22, wherein said processing channel further comprises a digital filter.

24. The ultrasonic diagnostic imaging system of claim 23, wherein said digital filter alternately exhibits two different passbands.

25. The ultrasonic diagnostic imaging system of claim 24, wherein said digital filter alternately exhibits a high frequency passband which produces harmonic frequency signal components, and a low frequency passband which produces fundamental frequency signal components.

26. A method for producing an ultrasonic image which is a blend of fundamental and harmonic frequency echo information comprising the steps of:

receiving from a range of depths a sequence of ultrasonic echoes from tissue of the body which contain both fundamental and harmonic frequency components;

separating said fundamental and harmonic frequency components of said ultrasonic echoes;

forming signals corresponding to said range of depths which are a varying composition of said fundamental and harmonic frequency components with depth; and displaying an image produced from said signals.

27. A method for producing an ultrasonic image which is a blend of fundamental and harmonic frequency echo information comprising the steps of:

receiving from a range of depths a sequence of ultrasonic echoes from tissue of the body which contain both fundamental and harmonic frequency components;

separating said fundamental and harmonic frequency components of said ultrasonic echoes;

forming signals corresponding to said range of depths which are a varying composition of said fundamental and harmonic frequency components; and displaying an image produced from said signals, wherein said step of forming forms signals primarily composed of harmonic frequency information at a shallow depth, and forms signals primarily composed of fundamental frequency information at a deeper depth.

28. An ultrasonic imaging method comprising:

transmitting ultrasonic energy to a target, said ultrasonic energy characterized by a peak power level in a fundamental frequency band;

receiving ultrasonic echo information associated with said transmitted ultrasonic energy in first and second frequency bands, said first frequency band comprising said fundamental frequency band, said second frequency band comprising a harmonic of said fundamental frequency band and substantially excluding said fundamental frequency band;

forming a composite image in response to said received ultrasonic echo information, said composite image comprising spatially distinct near-field and far-field regions, said far-field region emphasizing echo information in the first frequency band and said near-field region emphasizing echo information in the second band.

29. An ultrasonic imaging method comprising the following steps:

(a) acquiring fundamental mode ultrasonic image signals and harmonic mode ultrasonic image signals from a scanned region with a transducer;

(b) combining the fundamental and harmonic mode image signals of step (a) to form a composite image, said composite image comprising a first predetermined image region that is modulated primarily as a function of the fundamental mode ultrasonic image signals and a second predetermined image region that is modulated primarily as a function of the harmonic mode ultrasonic image signals.

30. The ultrasonic imaging method of claim 29, wherein acquiring harmonic mode ultrasonic image signals is performed in the absence of an ultrasonic contrast agent in the scanned region.

31. A medical ultrasonic diagnostic composite image comprising:

a first predetermined image region modulated primarily as a function of fundamental mode ultrasonic image signals acquired from a portion of a subject;

a second predetermined image region modulated primarily as a function of harmonic mode ultrasonic image signals acquired from a portion of the subject.

32. The medical ultrasonic diagnostic composite image of claim 31, wherein the harmonic mode ultrasonic image signals are acquired in the absence of an ultrasonic contrast agent.

33. An ultrasonic imaging system comprising:

means for acquiring fundamental mode ultrasonic image signals and harmonic mode ultrasonic image signals from a scanned region with a transducer;

means for combining the fundamental and harmonic mode image signals to form a composite image, said composite image comprising a first predetermined image region that is modulated primarily as a function of the fundamental mode ultrasonic image signals and a second predetermined image region that is modulated primarily as a function of the harmonic mode ultrasonic image signals.

34. The ultrasonic imaging system of claim 33, wherein the means for acquiring acquires the harmonic mode ultrasonic image signals in the absence of an ultrasonic contrast agent in the scanned region.

35. An ultrasonic imaging method comprising the following steps:
   (a) acquiring fundamental mode ultrasonic image signals and harmonic mode ultrasonic image signals with a transducer;
   (b) combining the fundamental and harmonic mode image signals of step (a) to form a composite image, said composite image comprising a first image region that is modulated primarily as a function of the fundamental mode ultrasonic image signals, a second image region that is modulated primarily as a function of the harmonic mode ultrasonic image signals, and a compound image region that is modulated as a function of both the fundamental mode image signals and the harmonic mode image signals, the compound region being intermediate of the first and second image regions.

36. The ultrasonic imaging method of claim 35, wherein the step of acquiring further comprises acquiring harmonic mode ultrasonic image signals in the absence of an ultrasonic contrast agent.

37. A medical ultrasonic diagnostic imaging system adapted to provide a composite image comprising:
   a first image region modulated primarily as a function of fundamental mode ultrasonic image signals;
   a second image region modulated primarily as a function of harmonic mode ultrasonic image signals; and
   a compounded region, intermediate the first and second image regions, said compounded region modulated as a function of both the fundamental mode image signals and the harmonic mode image signals.

38. The medical ultrasonic diagnostic imaging system of claim 37, wherein the harmonic mode ultrasonic image signals are acquired in the absence of an ultrasonic contrast agent.

39. An ultrasonic imaging method comprising the following steps:
   (a) acquiring fundamental mode ultrasonic image signals and harmonic mode ultrasonic image signals with a transducer in the absence of an ultrasonic contrast agent;
   (b) combining the fundamental and harmonic mode image signals of step (a) to form a composite image, said composite image comprising a first image region that is modulated as a function of the fundamental mode ultrasonic image signals and a second image region that is modulated primarily as a function of the harmonic mode ultrasonic image signals.

40. A medical ultrasonic diagnostic imaging system adapted to provide a composite image of a subject comprising:
   a first image region modulated primarily as a function of fundamental mode ultrasonic image signals acquired from a first region of the subject; and
   a second image region modulated primarily as a function of harmonic mode ultrasonic image signals acquired from a second region of the subject in the absence of an ultrasonic contrast agent.

41. An ultrasonic imaging system comprising:
   means for acquiring fundamental mode ultrasonic image signals and harmonic mode ultrasonic image signals with a transducer in the absence of an ultrasonic contrast agent;
   means for combining the fundamental and harmonic mode image signals to form a composite image, said composite image comprising a first image region that is modulated primarily as a function of the fundamental mode ultrasonic image signals and a second image region that is modulated primarily as a function of the harmonic mode ultrasonic image signals.

* * * * *